US009190844B2

(12) United States Patent
Tran

(10) Patent No.: US 9,190,844 B2
(45) Date of Patent: Nov. 17, 2015

(54) SYSTEMS AND METHODS FOR REDUCING ENERGY USAGE

(71) Applicant: Bao Tran, Saratoga, CA (US)

(72) Inventor: Bao Tran, Saratoga, CA (US)

( * ) Notice: Subject to any disclaimer, the term of this patent is extended or adjusted under 35 U.S.C. 154(b) by 520 days.

(21) Appl. No.: 13/668,302

(22) Filed: Nov. 4, 2012

(65) Prior Publication Data

US 2014/0129160 A1 May 8, 2014

(51) Int. Cl.
*G06F 19/00* (2011.01)
*H02J 3/14* (2006.01)

(52) U.S. Cl.
CPC .............. *H02J 3/14* (2013.01); *G06F 19/3418* (2013.01)

(58) Field of Classification Search
USPC .......................................................... 702/61
See application file for complete search history.

(56) References Cited

U.S. PATENT DOCUMENTS

| | | |
|---|---|---|
| 4,858,141 A | 8/1989 | Harts |
| 5,168,170 A | 12/1992 | Hartig |
| 5,483,153 A | 1/1996 | Leeb |
| 7,002,463 B2 | 2/2006 | Wakabayashi |
| 7,693,670 B2 | 4/2010 | Durling |
| 8,195,313 B1 | 6/2012 | Farrell et al. |
| 2005/0171645 A1 | 8/2005 | Oswald |
| 2009/0063201 A1 | 3/2009 | Nowotarski |
| 2009/0307178 A1 | 12/2009 | Kuhns |
| 2010/0082174 A1 | 4/2010 | Weaver |
| 2010/0085894 A1 | 4/2010 | Johnson |
| 2011/0106471 A1 | 5/2011 | Curtis et al. |

OTHER PUBLICATIONS

Mario Berges, Learning Systems for Electric Consumption of Buildings, Proceedings of the 2009 ASCE International Workshop on Computing in Civil Engineering, Austin, Texas. pp. 1-10.*
Mario Berges, Learning Systems for Electric Consumption of Buildings, Proceedings of the 2009 ASCE International Workshop on Computing in Civil Engineering, Austin, Texas.
Tobias Hochwallner, Approaches for Monitoring and Reduction of Energy Consumption in the Home, Seminar-Thesis: Lecture Series on Sustainable Development and Information and Communication Technology, Jun. 30, 2009.
Jennifer M. Urban, Comments of the Center for Democracy & Technology, Center for Democracy & Technology, Dec. 1, 2009.
Vernon A. Smith, Final Report Compilation for Equipment Scheduling and Cycling, California Energy Commission, Oct. 2003.
S. Kondepudi, Low Cost NIALAMS Technology, Electric Power Research Institute, Sep. 1997.
VTC Tech. Res. Ctr Finland, Foresight Reflections to 2025, Jul. 23, 2010.
David J. Leeds, The Smart Grid in 2010: Market Segments, Applications and Industry Players, Greentech Media Inc, 2009.
W K Lee, Exploration on Load Signatures, International Conference on Electrical Engineering, 2004, Japan.

(Continued)

*Primary Examiner* — Tung S Lau
(74) *Attorney, Agent, or Firm* — Tran & Associates

(57) ABSTRACT

A system for detecting individual appliance energy loads from a building composite load profile includes an electric meter to capture building composite load profile; a detector coupled to the meter to detect transitions in the load profile to determine an appliance state machine for each appliance; a clusterizer to detect clusters of patterns in the load profile; and an analyzer coupled to the detector to receive the transitions and appliance state machines from the detector, the analyzer matching each transition to a predetermined appliance state machine to disaggregate the building composite load profile into individual appliance energy loads.

20 Claims, 5 Drawing Sheets

(56) References Cited

OTHER PUBLICATIONS

Xiaofan Jiang, Design and Implementation of a High-Fidelity AC Metering Network, Apr. 15-18, 2009.

Jonathan Koomey, The Role of Building Technologies in Reducing and Controlling Peak Electricity Demand, Energy Analysis Department Environmental Energy Technologies Division Ernest Orlando Lawrence Berkeley National Laboratory, Sep. 2002.

K. D. Lee, High Performance Commercial Building Systems, Massachusetts Institute of Technology, Oct. 8, 2001.

Kwangduk Douglas Lee, Estimation of Variable-Speed-Drive Power Consumption From Harmonic Content, IEEE Transactions on Energy Conversion, vol. 20, No. 3, Sep. 2005.

Mario Berges, Training Load Monitoring Algorithms on Highly Sub-Metered Home Electricity Consumption Data, Tsinghua Science and Technology ISSN 1007-0214 65/67 pp. 406-411 vol. 13, No. S1, Oct. 2008.

Steven B. Leeb, Development and Validation of a Transient Event Detector, AMP Journal of Technology vol. 3 Nov. 1993.

K. D. Lee, Development of a Functioning Centrally Located Electrical-Load Monitor, Public Interest Energy Research (PIER) Program Energy-Efficient and Affordable Small Commercial and Residential Buildings California Energy Commission Contract 400-99-011, May 27, 2003.

Kwanduk Douglas Lee, Electric Load System Based on Non-Intrusive Power Monitoring, Thesis submitted to MIT Department of Mechanical Engineeering, May 23, 2003.

Michael Baranski, Non-Intrusive Appliance Load Monitoring based on an Optical Sensor, Bologna PowerTech Conference, Jun. 23-26, 2003, Bologna, Italy.

Alan Marchiori, Using Circuit-Level Power Measurements in Household Energy Management Systems, Department of Mathematical and Computer Sciences Colorado School of Mines Nov. 3, 2009.

Christopher Loughman, Advanced Nonintrusive Monitoring of Electric Loads, High Performance Commercial Building Systems, Mar./Apr. 2003, pp. 56-63.

Steve Selkowitz, Non-Intrusive Load Monitors (NILMs) used for Equipment Monitoring and Fault Detection, Technical Report for Cal. Energy Commission, Oct. 2003.

Elias Leake Quinn, Smart Metering & Privacy: Existing Law and Competing Policies, Colorado Public Utilities Commission, Spring 2009.

Elias L. Quinn, Privacy and The New Energy Infrastructure, 2009.

Pepco Inc., Business Case in Support of PEPCO's Blueprint for the Future Application, Dec. 2007.

David C. Bergman, Non-Intrusive Load Shed Verification, 2009.

The Energy Detective, Inc., TED-5000 Footprints User Manual, 2009.

Dr. Hampden Kuhns, Utility Accountant: Energy Management by Load Disaggregation, Desert Research Institute, Division of Atmospheric Sciences, Reno NV 2009.

Jon Froehlich, Disaggregated End-Use Energy Sensing for the Smart Grid, IEEE Pervasive Computing, Special Issue on Smart Energy Systems, to appear in Jan.-Mar. 2011 issue.

Sidhant Gupta, ElectriSense: Single-Point Sensing Using EMI for Electrical Event Detection and Classification in the Home, UbiComp 2010, Sep. 26-29, 2010, Copenhagen, Denmark.

Younghun Kim, ViridiScope: Design and Implementation of a Fine Grained Power Monitoring System for Homes, Ubicomp 2009, Sep. 30-Oct. 3, 2009, Orlando, Florida, USA.

* cited by examiner

| |
|---|
| detect wake-up time in the daily activity patterns (201) |
| detect calling time in the daily activity patterns (202) |
| detect toilet-using time in the daily activity patterns by detecting that the electric lamp in the toilet is turned on/off and a low volume of water consumption rate (203) |
| detect entertainment pattern (204) |
| detect bathing time in the daily activity patterns by detecting a high volume of water consumption rate and that the electric lamp in the bathroom is turned on (205) |
| detect cooking time or time in kitchen(206) |
| detect room-to-room movement (207) |

FIG. 3

SYSTEMS AND METHODS FOR REDUCING ENERGY USAGE

The present application claims priority to U.S. application Ser. No. 12/871,638, filed Aug. 30, 2010, the content of which is incorporated by reference.

BACKGROUND

The present invention relates to reducing building energy use.

Improvements in living condition and advances in health care have resulted in a marked prolongation of life expectancy for elderly and disabled population. These individuals, a growing part of society, are dependent upon the delivery of home health and general care, which has its own set of challenges and drawbacks. This population needs continuous general, as well as medical, supervision and care.

The bulk of residential energy consumption is devoted to space heating and cooling. Unlike other end uses, households typically have direct control over the amount of heating or cooling used in their home. Unfortunately, energy consumption is typically reported as a "lump sum" rather than being allocated to specific devices or end uses. Even advanced metering systems that record energy use by day, hour, or even minute, only report the aggregate usage for each household.

United States Patent Application 20110106471 discloses a method and system for disaggregating climate control energy use from non-climate control energy use for a building. The method includes receiving a series of building energy use values and corresponding outdoor temperature values for a time period. Each of the energy use values and outdoor temperature values is associated with a time interval. The method further includes determining a series of temperature difference values for the time period based on a difference in temperature between a predetermined baseline temperature and each of the outdoor temperature values. A regression analysis is used to determine a climate control coefficient and a non-climate control coefficient from the energy use values and temperature difference values. The climate control coefficient and/or the non-climate control coefficient are used to determine climate control energy use and/or non-climate control energy use for the building.

SUMMARY

In one aspect, a system for detecting individual appliance energy loads from a building composite load profile includes an electric meter to capture building composite load profile; a detector coupled to the electric meter to detect transitions in the load profile to determine an appliance state machine for each appliance; a clusterizer to detect clusters of patterns in the load profile; and an analyzer coupled to the detector to receive the transitions and appliance state machines from the detector, the analyzer matching each transition to a predetermined appliance state machine to disaggregate the building composite load profile into individual appliance energy loads.

In another aspect, a method for detecting individual appliance energy loads from a building composite load profile includes determining transitions within the building composite load profile; clusterizing patterns in the load profile and determining specific appliance state machines for each appliance in the building based on the clusterized patterns; and disaggregating the building composite load profile into individual appliance energy loads by assigning the determined transitions to the determined specific appliance state machines.

In yet another aspect, a method of improving energy efficiency includes determining an appliance load signature from a user's existing appliance, determined from a building composite load signature; determining a substitute appliance for the existing appliance; and presenting to the user cost savings between the user's existing appliance and the substitute appliance.

In another aspect, a device such as a thermostat or a cellular telephone includes a wireless transceiver coupled to a utility meter to receive building composite load profile; a detector coupled to the wireless transceiver to detect transitions in the load profile to determine an appliance state machine for each appliance; a clusterizer to detect clusters of patterns in the load profile; and an analyzer coupled to the detector to receive the transitions and appliance state machines from the detector, the analyzer matching each transition to a predetermined appliance state machine to disaggregate the building composite load profile into individual appliance energy loads.

In a further aspect, a system for reducing energy usage includes one or more utility meters each capturing energy load data on a fifteen minute data interval or an hourly basis; a usage disaggregator coupled to one or more of the utility meters to disaggregate energy consumption for one or more predetermined appliances based on the data interval (such interval can be 15 minutes interval, 30 minutes interval, or hourly interval, among others) electrical load signatures of each predetermined appliance; and an energy messaging module coupled to the energy usage disaggregator to help users reduce energy consumption.

In another aspect, a method to reduce energy usage includes reading fifteen minute interval or hourly interval energy load data from utility meters; disaggregating energy consumption for each of predetermined appliances from the interval of energy load data; and normatively messaging users to reduce energy consumption.

In yet another aspect, a system for optimizing energy usage includes one or more utility meters to generate electrical load data at a 15-minute interval or hourly interval; a load monitoring disaggregator receiving the interval of electrical load data from the utility meters to identify power consumption from each of predetermined appliances; and an energy messaging module coupled to the disaggregator to generate normative energy saving messages to users.

Implementations of the system can enable energy consumers to increase energy efficiency, reduce costs, and realize environmental benefits. The system can:
- Collect detailed occupancy/usage data with a combination of sub-meters and low cost sensors
- Create models of occupancy patterns (Daily Office Activities)
- Visualize usage data
- Apply occupancy models with sensor data to automatically control HVAC/heating/lighting/appliances to save energy
- Predict demand and communicate with utility computers during peak load
- Prompting of building occupants for energy-saving actions.

Advantages of the system may include one or more of the following. Once the system can create accurate energy usage models for the building and its occupants, the system applies normative messaging to successfully engage and motivate action across a very high percentage of targeted individuals. The normative message motivates office workers to take action which is one of the main challenges to achieving large scale energy savings. Participation rates in most energy-efficiency programs are typically less than 5%. By contrast, the messaging system achieves much higher energy-saving actions by presenting users with only relevant and immediately actionable suggestions on how to cut down power consumption in their immediate office/cubicle. The system leverages behavioral science, customer data analytics, and the latest software to engage employees of utilities and energy consumers to collectively take action to save energy.

BRIEF DESCRIPTION OF THE DRAWINGS

FIG. 3 illustrates a process for classifying daily life activities.

DESCRIPTION

Figure 1:
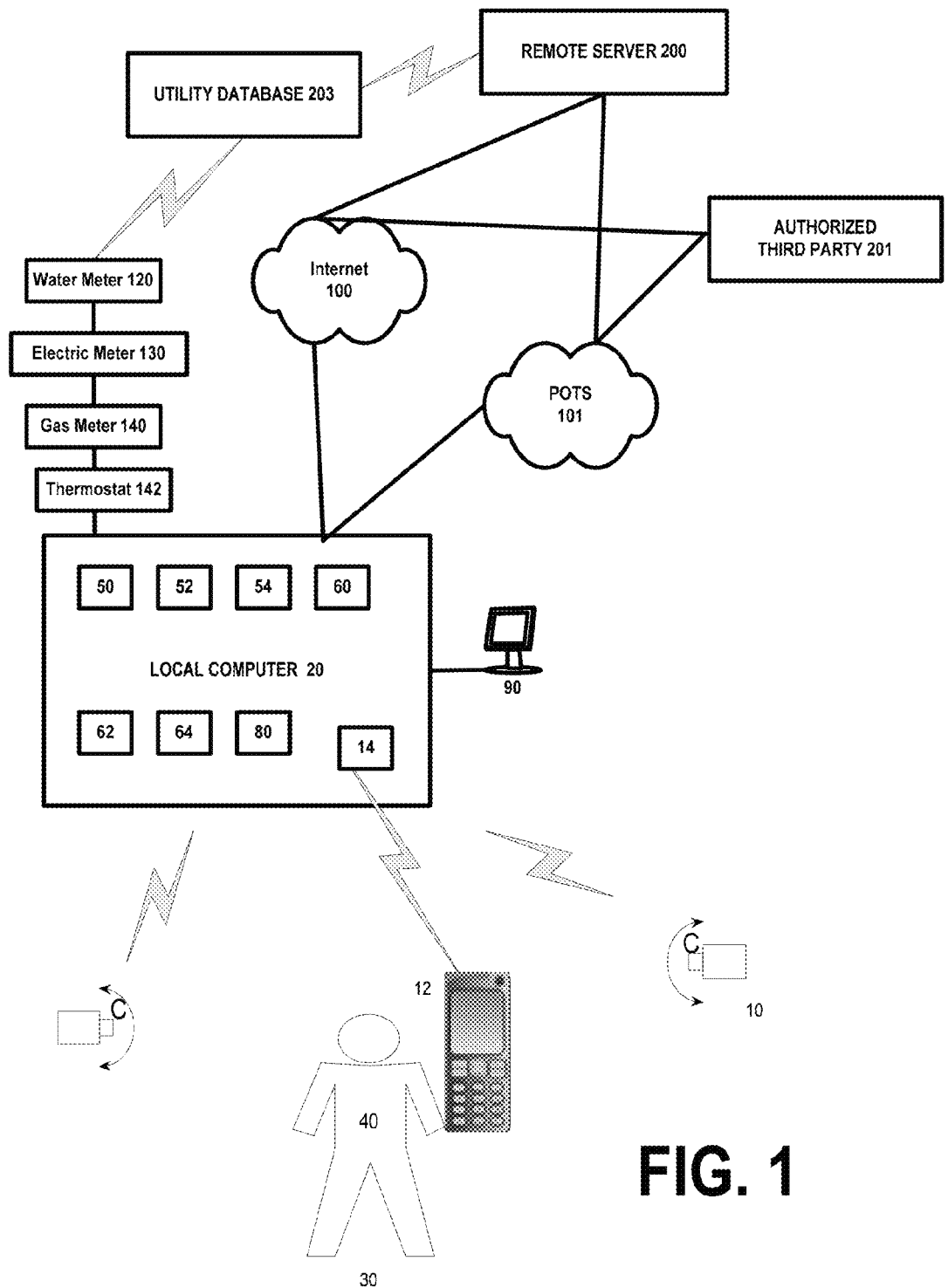
FIG. 1 illustrates an exemplary embodiment for monitoring energy usage.

FIG. 1 shows an exemplary home energy monitoring system. In this system, a plurality of monitoring cameras 10 are placed in various predetermined positions in a home of a patient 30. The cameras 10 can be wired or wireless. For example, the cameras can communicate over infrared links or over radio links conforming to the 802.11X (e.g. 802.11A, 802.11B, 802.11G) standard or the Bluetooth standard to a server 20. The server 20 stores images and videos of family members or elderly patients 30.

In one embodiment, electric/gas/water consumption can be monitored. This approach non-invasively infers user activities through the operations of appliances during the day. For example, in the morning, a user may use a toaster and turn on a TV for news. The user may also turn on lights in the bathrooms and use water for toiletry and bathing purposes. The user may then turn on a computer and conduct business using the telephone or cell phone. Periodically, the user may use the fan or AC or heater as needed. The user may also use the oven/stove and the kitchen sink for lunch/dinner preparation. In this brief example, electricity, gas and water is consumed. The embodiment captures data associated with electricity, gas and water consumption for modeling user daily activities, and abnormality in daily activity can be detected non-invasive manner without requiring the user to wear sensors. Further, this solution is inexpensive since it can operate off meters which are installed free by utilities. For example, smart electric meters uses programmable solid-state meter technology that provides two-way communication between the meter at the home or business and the utility, using secure wireless network technology. The solid-state digital SmartMeter™ from PG&E is an electric meter that records hourly meter reads and periodically transmits the reads via a dedicated radio frequency (RF) network back to PG&E. Each SmartMeter™ electric meter is equipped with a network radio, which transmits meter data to an electric network access point (pictured below). The system uses RF mesh technology, which allows meters and other sensing devices to securely route data via nearby meters and relay devices, creating a "mesh" of network coverage. The system supports two-way communication between the meter and PG&E. The electric network access point collects meter data from nearby electric meters and periodically transfers this data to PG&E via a secure cellular network. Each RF mesh-enabled device (meters, relays) is connected to several other mesh-enabled devices, which function as signal repeaters, relaying the data to an access point. The access point device aggregates, encrypts, and sends the data back to PG&E over a secure commercial third-party network. The resulting RF mesh network can span large distances and reliably transmit data over rough or difficult terrain. If a meter or other transmitter drops out of the network, its neighbors find another route. The mesh continually optimizes routing to ensure information is passed from its source to its destination as quickly and efficiently as possible.

The gas system uses point-to-point RF technology to transmit gas usage data from SmartMeter™ gas modules back to PG&E over a dedicated, secure wireless network. Due to the simpler data requirements of the gas system, the SmartMeter™ gas system supports only one-way communication from customers to PG&E. PG&E attaches the SmartMeter™ gas module to the traditional gas meter. This module is outfitted with a radio frequency (RF) transmitter. The module records daily meter reads and then uses an RF signal to transmit the reads to a data collector unit (see below) in the vicinity. The data collector unit (DCU), in turn, collects meter reads from many meters and securely transmits the gas usage data over a secure wireless network back to PG&E. Similarly, water meter can be digitized.

Various types of information contained in the collected data can be used to identify a particular activity of life. For example measurements can be made of: the time the consumption began; the duration of the consumption; the rate of consumption; the total amount of utility consumed during a particular period; the maximum or peak use; the shape and magnitude of the electrical power waveform (such as the 60 Hz waveform); and any changes in the rate of consumption. These measurements can be compared to a library of standard values for different types of loads. The measurements can also be compared to a library of appliances previously observed on the utility signal. As an example of how consumption can be used to identify a load, a toilet flush can be distinguished from a shower based on the duration of the consumption, the total amount of water consumed, and the water flow rate.

Time of day information can sometimes assist in identifying a life activity. For example water usage in the middle of the night is more likely to be due to a toilet flush than a shower. Even if the consumption patterns are not sufficient to completely identify the loads, they can still be used to help select the most likely candidates. The user can assist the appliance identification program by linking an unidentified appliance to the name of an appliance that is known have been in operation.

Figure 2A:
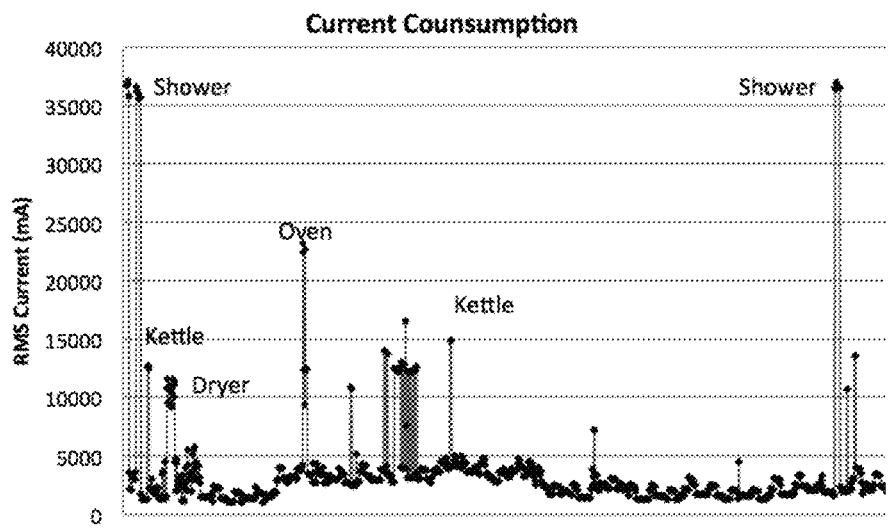
FIG. 2A shows an exemplary energy consumption for various appliances over a period of time.
Figure 2B:
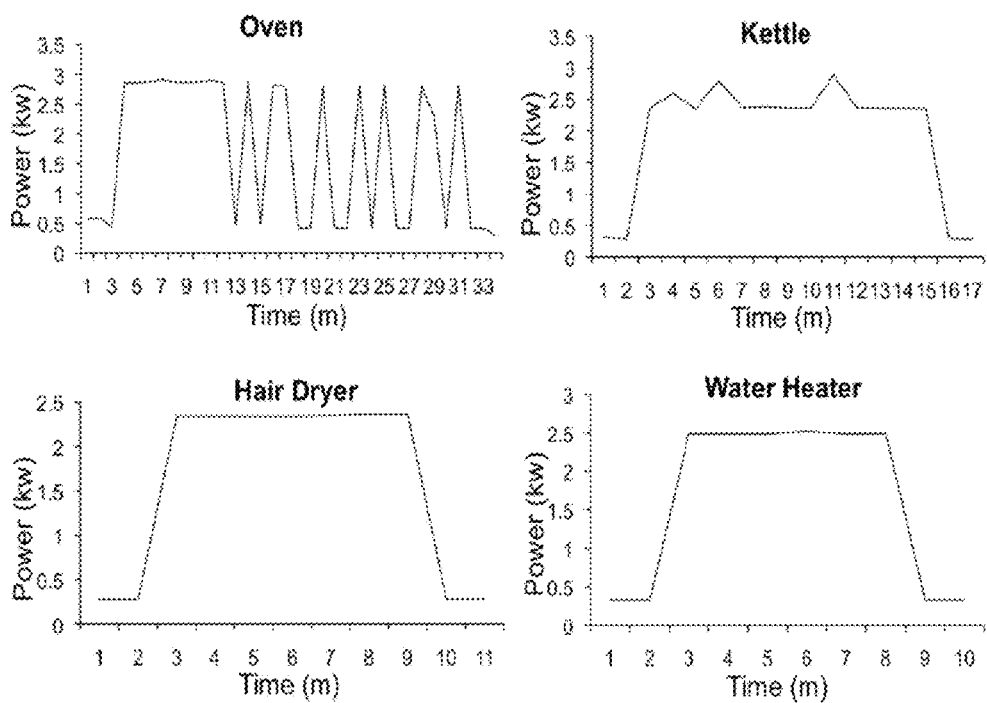
FIG. 2B shows exemplary signatures for various appliances.
Figure 2C:
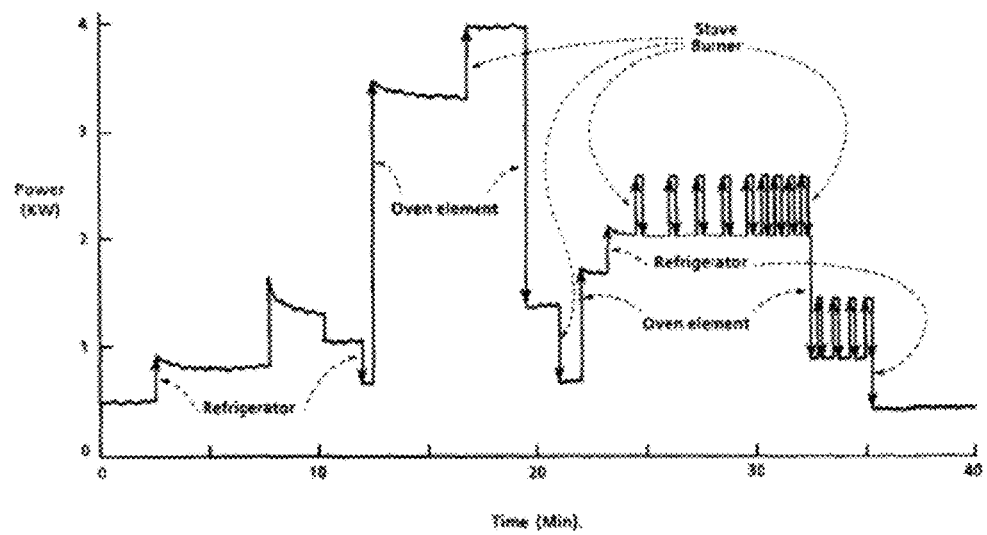
FIG. 2C shows exemplary step changes in the power verses time plot due to individual appliance events.
Figure 2D:
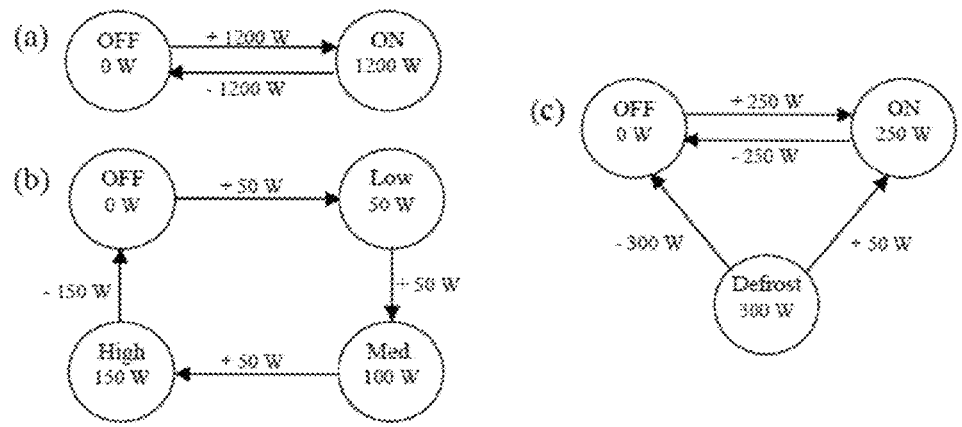
FIG. 2D shows an exemplary state transition tables or models for a two state appliance such as a toaster, a two state appliance such as a three way lamp, and a refrigerator with a defrost state, respectively.

FIG. 2A shows an exemplary energy consumption chart for various appliances over a period of time while FIG. 2B shows various exemplary signatures for an electric oven, hair dryer, water heater and kettle. FIG. 2C shows exemplary step changes in the power verses time plot due to individual appliance events. FIG. 2D shows an exemplary state transition tables or models for a two state appliance such as a toaster, a two state appliance such as a three way lamp, and a refrigerator with a defrost state, respectively.

From the signatures, the system can infer daily activity. When the data is electrical data, additional information may be measured and used to identify a load. For example, the shape and size of the 60 Hz conductance waveform (defined as the current divided by the voltage) may be used to help identify the load. Typical resistive appliances, such as incandescent lights and clothes irons, draw current that is in phase with the AC voltage. Appliances with a reactive and resistive load (such as a DC transformer for a stereo amplifier and a motor on a clothes washer) draw current that is out of phase with the voltage. Yet other appliances, such as computers, have switching power supplies that consume power for brief intervals during a voltage cycle. Analysis of the amplitude and temporal variation of the current and power waveforms can help identify specific loads connected to a circuit. The circuit can be characterized by its voltage and current measured at a particular sampling rate, such as 3840 Hz to provide 64 samples per voltage cycle.

For some loads, the current or voltage may be very stable. For example, certain light bulbs are either on or off. Other loads may operate at discrete values, such as a ceiling fan with 3 speeds. Further types of loads will have a range of settings, such as a power drill having variable speed control. Finally, other loads (such as a refrigerator, TV, or computer) may have more complex combinations of conductance over time. The system can include circuits for sampling the electrical power at the electrical power line and converting the sampled power into digital format to provide digital signals proportional to circuit load characteristics such as real power, reactive power, current, admittance, harmonics, sub-harmonics, dc current, starting-transient peak; starting-transient duration, starting-transient time-constant, or starting-transient shape. Signal processing techniques can be used to analyze the total household electrical or water use data, into particular daily activities based on the unique properties of each load. A library of properties of common loads can be maintained and accessed by the user interface, user computer, or remote system. For example, the library can include properties of appliances from model years that are most likely to be used in the monitored environment.

When located on the user interface or user computer, this library can be updated periodically, such as through the internet by the remote server. Other programming of the user interface, or software running on the user computer, can also be updated via the internet, such as with improved algorithms, heuristics, and the like. In certain implementations, training or other user provided data is used to update a library that can be shared with other users. With a broad set of load profiles, the systems will be able to, in particular examples, automatically identify the loads consuming the majority of the utilities in the monitored area.

In some aspects, the systems use a processing algorithm that employs statistical analysis, such as a least squares fit, to identify individual loads. In a specific example, an effective variance analysis is performed on changes in conductance. Conductance is a useful parameter to characterize the power consumption behavior of an appliance since it is: (1) voltage independent (i.e. an appliance's conductance changes minimally with normal fluctuations in voltage delivered to the circuit) and (2) is additive for the calculation of power (i.e. the conductance on a circuit is the sum of the conductances of all appliances).

In some examples, the voltage and current waveform is sampled at a sufficient rate such that many data points are collected for each voltage period. When the AC voltage V passes from negative to positive, current I and voltage V data points are each inserted into the first columns of a two dimensional array. The number of rows in the array is defined by the number of samples taken during a voltage cycle. When the AC voltage V passes from negative to positive again, the current and voltage data are inserted into the next columns of the arrays and so forth. With this data, instantaneous values of the Power P (I*V) measured in Watts and Conductance G (I/V) measured in Siemens can be calculated.

As noted above, the hardware for non-invasive monitoring is minimal. In some configurations, meters 120, 130, 140 are directly connected to the user interface 90, or local computer 20, such as through a wired connection, including standard communication protocols and adapters such as RS-232, Ethernet, serial, parallel port, SPI, SCSI, I2C, ZigBee, and USB connections. In a particular example, the utility meters 120, 130, 140 send signals to the user interface 90 over power lines, such as using a power line modem. The components of the system communicate may use the X10 communication standard. Utility meters 120, 130, and 140 can generate wireless signals received over the LAN or WAN and then displayed by user interface 90 or processed on local computer 20. In some implementations, the user computer accesses the user interface 90 through a web browser. For example, the user interface 90 may be assigned an internet protocol (IP) address. In particular examples, the user interface 90 communicates with the user computer 160, remote system 170, or network 180 over the Internet.

In particular embodiments, adapters can be hooked, mounted or installed with the meters 120, 130 and 140 by a consumer or other end users such as a professional electrician or plumber. Suitable electrical meter adapters can include the Meter Interface Units (MIUs) available from Archnet of ShenZhen, China. In some implementations, the electrical adapter for electricity meter 130 can be an in line shunt resistor, a current transducer, or a Hall Effect sensor. Suitable Hall Effect sensors are available from GMW Associates of San Carlos, Calif., such as the Sentron CSA-1V. The water meter adapter can be a photo sensor, such as an infrared or optical sensor, that detects rotation of a dial mechanism. In one example, the sensor detects reflection of light off of the dial mechanism. A light source, such as an optical or infrared LED, is included, in certain embodiments, to generate a signal to be measured. An integrated light emitting diode and photodiode is available from Honeywell (PN# HOA1180). A marker, such as a piece of more highly light absorbing or reflecting material, may be placed on the dial in order to help track rotation of the dial. In further examples, a separate meter, such as a flow meter, is installed in the gas line or water line. A separate meter may also be included on the electrical line, such as a voltage or current meter. In particular implementations, the electrical adapter is installed between an electrical socket and an existing electrical meter, such as an electrical meter installed by a power company. Suitable socket adapters are available from RIOTronics, Inc. of Englewood, Colo. In some implementations, the adapters read signals, such as wireless signals, generated by an existing meter, such as a meter installed by a utility company.

In some implementations, the electrical adapter, or multiple electrical adapters, is connected to one or more individual circuits entering a measurement site. Each circuit may have a separate adapter, such as an electric metering device, or multiple circuits may be individually monitored by a single electrical adapter. In particular examples, the electrical adapter includes a current transducer (not shown) attached to the wires corresponding to each breaker switch in a circuit box. A multi-channel analog to digital voltage sensor may be in communication with the current transducer to simultaneously monitor multiple circuits.

The server 20 also executes one or more software modules to analyze data from the patient. A module 50 monitors the patient's vital signs such as ECG/EKG and generates warnings should problems occur. In this module, vital signs can be collected and communicated to the server 20 using wired or wireless transmitters. In one embodiment, the server 20 feeds the data to a statistical analyzer such as a neural network which has been trained to flag potentially dangerous conditions. The neural network can be a back-propagation neural network, for example. In this embodiment, the statistical analyzer is trained with training data where certain signals are determined to be undesirable for the patient, given his age, weight, and physical limitations, among others. For example, the patient's glucose level should be within a well-established range, and any value outside of this range is flagged by the statistical analyzer as a dangerous condition. As used herein, the dangerous condition can be specified as an event or a pattern that can cause physiological or psychological damage to the patient. Moreover, interactions between different vital signals can be accounted for so that the statistical analyzer can take into consideration instances where individually the vital signs are acceptable, but in certain combinations, the vital signs can indicate potentially dangerous conditions. Once trained, the data received by the server 20 can be appropriately scaled and processed by the statistical analyzer. In addition to statistical analyzers, the server 20 can process vital signs using rule-based inference engines, fuzzy logic, as well as conventional if-then logic. Additionally, the server can process vital signs using Hidden Markov Models (HMMs), dynamic time warping, or template matching, among others.

A module 52 monitors the patient ambulatory pattern and generates warnings should the patient's patterns indicate that the patient has fallen or is likely to fall. 3D detection is used to monitor the patient's ambulation. In the 3D detection process, by putting 3 or more known coordinate objects in a scene, camera origin, view direction and up vector can be calculated and the 3D space that each camera views can be defined.

In one embodiment with two or more cameras, camera parameters (e.g. field of view) are preset to fixed numbers. Each pixel from each camera maps to a cone space. The system identifies one or more 3D feature points (such as a birthmark or an identifiable body landmark) on the patient. The 3D feature point can be detected by identifying the same point from two or more different angles. By determining the intersection for the two or more cones, the system determines the position of the feature point. The above process can be extended to certain feature curves and surfaces, e.g. straight lines, arcs; flat surfaces, cylindrical surfaces. Thus, the system can detect curves if a feature curve is known as a straight line or arc. Additionally, the system can detect surfaces if a feature surface is known as a flat or cylindrical surface. The further the patient is from the camera, the lower the accuracy of the feature point determination. Also, the presence of more cameras would lead to more correlation data for increased accuracy in feature point determination. When correlated feature points, curves and surfaces are detected, the remaining surfaces are detected by texture matching and shading changes. Predetermined constraints are applied based on silhouette curves from different views. A different constraint can be applied when one part of the patient is occluded by another object. Further, as the system knows what basic organic shape it is detecting, the basic profile can be applied and adjusted in the process.

A module 80 communicates with a third party such as the police department, a security monitoring center, or a call center. The module 80 operates with a POTS telephone and can use a broadband medium such as DSL or cable network if available. The module 80 requires that at least the telephone is available as a lifeline support. In this embodiment, duplex sound transmission is done using the POTS telephone network. The broadband network, if available, is optional for high resolution video and other advanced services transmission.

During operation, the module 80 checks whether broadband network is available. If broadband network is available, the module 80 allows high resolution video, among others, to be broadcasted directly from the server 20 to the third party or indirectly from the server 20 to the remote server 200 to the third party. In parallel, the module 80 allows sound to be transmitted using the telephone circuit. In this manner, high resolution video can be transmitted since sound data is separately sent through the POTS network.

If broadband network is not available, the system relies on the POTS telephone network for transmission of voice and images. In this system, one or more images are compressed for burst transmission, and at the request of the third party or the remote server 200, the telephone's sound system is placed on hold for a brief period to allow transmission of images over the POTS network. In this manner, existing POTS lifeline telephone can be used to monitor patients. The resolution and quantity of images are selectable by the third party. Thus, using only the lifeline as a communication medium, the person monitoring the patient can elect to only listen, to view one high resolution image with duplex telephone voice transmission, to view a few low resolution images, to view a compressed stream of low resolution video with digitized voice, among others.

During installation or while no live person in the scene, each camera will capture its own environment objects and store it as background images, the software then detect the live person in the scene, changes of the live person, so only the portion of live person will be send to the local server, other compression techniques will be applied, e.g. send changing file, balanced video streaming based on change.

The local server will control and schedule how the video/picture will be send, e.g. when the camera is view an empty room, no pictures will be sent, the local server will also determine which camera is at the right view, and request only the corresponding video be sent. The local server will determine which feature it is interested in looking at, e.g. face and request only that portion be sent.

With predetermined background images and local server controlled streaming, the system will enable higher resolution and more camera system by using narrower bandwidth.

Through this module, a police officer, a security agent, or a healthcare agent such as a physician at a remote location can engage, in interactive visual communication with the patient. The patient's health data or audio-visual signal can be remotely accessed. The patient also has access to a video transmission of the third party. Should the patient experience health symptoms requiring intervention and immediate care, the health care practitioner at the central station may summon help from an emergency services provider. The emergency services provider may send an ambulance, fire department personnel, family member, or other emergency personnel to the patient's remote location. The emergency services provider may, perhaps, be an ambulance facility, a police station, the local fire department, or any suitable support facility.

Communication between the patient's remote location and the central station can be initiated by a variety of techniques. One method is by manually or automatically placing a call on the telephone to the patient's home or from the patient's home to the central station.

Alternatively, the system can ask a confirmatory question to the patient through text to speech software. The patient can be orally instructed by the health practitioner to conduct specific physical activities such as specific arm movements, walking, bending, among others. The examination begins during the initial conversation with the monitored subject. Any changes in the spontaneous gestures of the body, arms and hands during speech as well as the fulfillment of nonspecific tasks are important signs of possible pathological events. The monitoring person can instruct the monitored subject to perform a series of simple tasks which can be used for diagnosis of neurological abnormalities. These observations may yield early indicators of the onset of a disease.

A network 100 such as the Internet receives images from the server 20 and passes the data to one or more remote servers 200. The images are transmitted from the server 20 over a secure communication link such as virtual private network (VPN) to the remote server(s) 200.

The server 20 collects data from a plurality of cameras and uses the 3D images technology to determine if the patient needs help. The system can transmit video (live or archived) to the friend, relative, neighbor, or call center for human review. At each viewer site, after a viewer specifies the correct URL to the client browser computer, a connection with the server 20 is established and user identity authenticated using suitable password or other security mechanisms. The server 200 then retrieves the document from its local disk or cache memory storage and transmits the content over the network. In the typical scenario, the user of a Web browser requests that a media stream file be downloaded, such as sending, in particular, the URL of a media redirection file from a Web server. The media redirection file (MRF) is a type of specialized Hypertext Markup Language (HTML) file that contains instructions for how to locate the multimedia file and in what format the multimedia file is in. The Web server returns the MRF file to the user's browser program. The browser program then reads the MRF file to determine the location of the media server containing one or more multimedia content files. The browser then launches the associated media player application program and passes the MRF file to it. The media player reads the MRF file to obtain the information needed to open a connection to a media server, such as a URL, and the required protocol information, depending upon the type of medial content is in the file. The streaming media content file is then routed from the media server down to the user.

Next, the transactions between the server 20 and one of the remote servers 200 are detailed. The server 20 compares one image frame to the next image frame. If no difference exists, the duplicate frame is deleted to minimize storage space. If a difference exists, only the difference information is stored as described in the JPEG standard. This operation effectively compresses video information so that the camera images can be transmitted even at telephone modem speed of 64 k or less. More aggressive compression techniques can be used. For example, patient movements can be clusterized into a group of known motion vectors, and patient movements can be described using a set of vectors. Only the vector data is saved. During view back, each vector is translated into a picture object which is suitably rasterized. The information can also be compressed as motion information.

Next, the server 20 transmits the compressed video to the remote server 200. The server 200 stores and caches the video data so that multiple viewers can view the images at once since the server 200 is connected to a network link such as telephone line modem, cable modem, DSL modem, and ATM transceiver, among others.

In one implementation, the servers 200 use RAID-5 striping and parity techniques to organize data in a fault tolerant and efficient manner. The RAID (Redundant Array of Inexpensive Disks) approach is well described in the literature and has various levels of operation, including RAID-5, and the data organization can achieve data storage in a fault tolerant and load balanced manner. RAID-5 provides that the stored data is spread among three or more disk drives, in a redundant manner, so that even if one of the disk drives fails, the data stored on the drive can be recovered in an efficient and error free manner from the other storage locations. This method also advantageously makes use of each of the disk drives in relatively equal and substantially parallel operations. Accordingly, if one has a six gigabyte cluster volume which spans three disk drives, each disk drive would be responsible for servicing two gigabytes of the cluster volume. Each two gigabyte drive would be comprised of one-third redundant information, to provide the redundant, and thus fault tolerant, operation required for the RAID-5 approach. For additional physical security, the server can be stored in a Fire Safe or other secured box, so there is no chance to erase the recorded data, this is very important for forensic analysis.

The system can also monitor the patient's gait pattern and generate warnings should the patient's gait patterns indicate that the patient is likely to fall. The system will detect patient skeleton structure, stride and frequency; and based on this information to judge whether patient has joint problem, asymmetrical bone structure, among others. The system can store historical gait information, and by overlaying current structure to the historical (normal) gait information, gait changes can be detected.

The system also provides a patient interface 90 to assist the patient in easily accessing information. In one embodiment, the patient interface includes a touch screen; voice-activated text reading; one touch telephone dialing; and video conferencing. The touch screen has large icons that are pre-selected to the patient's needs, such as his or her favorite web sites or application programs. The voice activated text reading allows a user with poor eye-sight to get information from the patient interface 90. Buttons with pre-designated dialing numbers, or video conferencing contact information allow the user to call a friend or a healthcare provider quickly.

In one embodiment, medicine for the patient is tracked using radio frequency identification (RFID) tags. In this embodiment, each drug container is tracked through an RFID tag that is also a drug label. The RF tag is an integrated circuit that is coupled with a mini-antenna to transmit data. The circuit contains memory that stores the identification Code and other pertinent data to be transmitted when the chip is activated or interrogated using radio energy from a reader. A reader consists of an RF antenna, transceiver and a microprocessor. The transceiver sends activation signals to and receives identification data from the tag. The antenna may be enclosed with the reader or located outside the reader as a separate piece. RFID readers communicate directly with the RFID tags and send encrypted usage data over the patient's network to the server 20 and eventually over the Internet 100. The readers can be built directly into the walls or the cabinet doors.

In one embodiment, capacitively coupled RFID tags are used. The capacitive RFID tag includes a silicon microprocessor that can store 96 bits of information, including the pharmaceutical manufacturer, drug name, usage instruction and a 40-bit serial number. A conductive carbon ink acts as the tag's antenna and is applied to a paper substrate through conventional printing means. The silicon chip is attached to printed carbon-ink electrodes on the back of a paper label, creating a low-cost, disposable tag that can be integrated on the drug label. The information stored on the drug labels is written in a Medicine Markup Language (MML), which is based on the eXtensible Markup Language (XML). MML would allow all computers to communicate with any computer system in a similar way that Web servers read Hyper Text Markup Language (HTML), the common language used to create Web pages.

After receiving the medicine container, the patient places the medicine in a medicine cabinet, which is also equipped with a tag reader. This smart cabinet then tracks all medicine stored in it. It can track the medicine taken, how often the medicine is restocked and can let the patient know when a particular medication is about to expire. At this point, the server 20 can order these items automatically. The server 20 also monitors drug compliance, and if the patient does not remove the bottle to dispense medication as prescribed, the server 20 sends a warning to the healthcare provider.

FIG. 3 shows an exemplary process to non-invasively infer daily life activities. Although the detection needs not be done in any particular order, an exemplary sequence is discussed. In one implementation, the process detects wake-up time in the daily activity patterns in 201. For example, the wake-up time may be detected by detecting existence of a person on a bed by using a pyroelectric infrared sensor, detecting that a television set is turned on in the morning or detecting electrical activities in the restroom in the morning. In another example, the bedtime may be detected by detecting that the television set is turned off at night or detecting the electric lamp being turned off in the bedroom. A telephone time detection 202 detects calling time in the daily activity patterns by receiving and analyzing phone bills or alternatively each time a phone is used, the phone transmits a log to the monitoring server to indicate the time when the person to be observed is using the phone. A toilet time detection 203 detects toilet-using time in the daily activity patterns by detecting that the electric lamp in the toilet is turned on/off and a low volume of water consumption rate. An entertainment time detection 204 detects TV watching time in the daily activity patterns by receiving and analyzing TV display power consumption or alternatively when stereo equipment is on. A bathing time detection 205 detects bathing time in the daily activity patterns by detecting a high volume of water consumption rate and that the electric lamp in the bathroom is turned on. A cooking time detection 206 detects cooking time in the daily activity patterns and is comprised of one or more sensors or one or more home electric appliances for detecting the time when the person to be observed is cooking. For example, the cooking time may be detected by detecting that a rice cooker or microwave oven is turned on/off, detecting that a gas range or an IH (Induction-Heating) cooking heater is turned on/off or detecting other cooking home electric appliances are turned on/off.

A room-to-room movement frequency detection 207 detects the number of movement between rooms in the daily activity patterns and is comprised of one or more sensors or one or more home electric appliances for detecting the number of movement between the rooms. For example, the number of movement between the rooms may be detected by detecting that the electric lamps in each room are turned on/off or detecting that other home electric appliances in each room are turned on/off.

Data of the daily activity patterns is detected by these detection sensors and transmitted to the data processing apparatus in a wireless or wired manner and, then, the transmitted data is stored in databases of the data processing apparatus. Every time the data processing apparatus receives the data of the daily activity patterns from the detection sensors, it performs the statistical analyses of the stored data so as to determine whether the received daily activity pattern is abnormal or not. If it is determined that the received daily activity pattern is abnormal, the reporting apparatus in the home of the person to be observed or the reporting apparatuses are informed of the abnormality. In response to the abnormality notification, the person to be observed or the observers checks whether the abnormality notification is correct or not and gives the data processing apparatus feedback about whether the abnormality notification is correct or not. Based on the feedback information, the data processing apparatus determines whether the daily activity patterns that have been considered abnormal correspond to the actual abnormalities or not and learns the daily activity patterns unique to the person to be observed. Here, although examples of the sensors for detecting the daily activity patterns include only the wake-up time detection, the bedtime detection, the toilet time detection, the room cleaning time detection, the bathing time detection, the cooking time detection and the room-to-room movement frequency detection as described above, other sensors for detecting the daily activity patterns may be provided.

For example, if the user typically sleeps between 10 pm to 6 am, the location would reflect that the user's location maps to the bedroom between 10 pm and 6 am. In one exemplary system with an optional heart rate monitor, the system builds a schedule of the user's activity as follows:

| Location | Time Start | Time End | Heart Rate |
|---|---|---|---|
| Bed room | 10pm | 6am | 60-80 |
| Gym room | 6am | 7am | 90-120 |
| Bath room | 7am | 7:30am | 85-120 |
| Dining room | 7:30am | 8:45am | 80-90 |
| Home Office | 8:45am | 11:30am | 85-100 |
| ... | | | |
| ... | | | |

Figure 4:
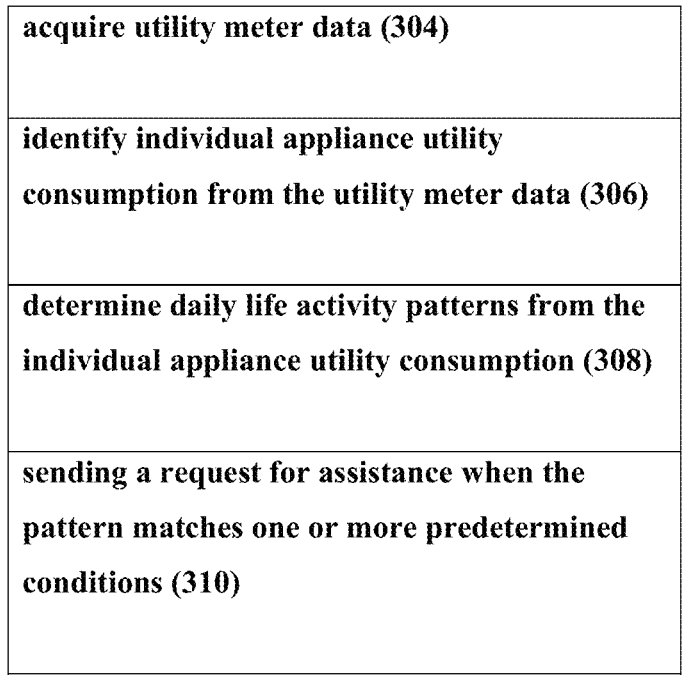
FIG. 4 shows an exemplary process to monitor a user.

FIG. 4 shows an exemplary process to monitor a patient. First, the process acquires utility meter data (304). In one embodiment, a direct data connection to a utility company database can be done. In another embodiment, sensors can be placed next to utility meters to get the data without having to get data from the utility company. Next, the process identifies individual appliance utility consumption from the utility meter data (306). The process then determines daily life activity patterns from the individual appliance utility consumption; and sending a request for assistance when the pattern matches one or more predetermined conditions (310).

The predetermined conditions can be dangerous conditions such as when a person has fallen, as detected by the 3D accelerometers, or indirectly such as when the patient is in the bathroom for an unusual period. The dangerous condition can include being in one position (such as bed or chair) for too long; having an oven on for an extended period, having the TV on without turning on lights in the bed room past a normal sleep time, or may be as simple as the cellphone being turned off for too long. The predetermined conditions can be programmed by a system installer, and may not relate to dangerous conditions, but simply conditions where someone such as a family member or a caretaker should follow up to ensure patient safety.

In one embodiment, the phone can simply request that the user shuts off an alarm countdown or acknowledge that the patient is doing ok to prevent false alarms. The daily life activity tracking is adaptive in that it gradually adjusts to the user's new activities and/or habits. If there are sudden changes, the system flags these sudden changes for follow up. For instance, if the user spends three hours in the bathroom, the system prompts the third party (such as a call center) to follow up with the patient to make sure he or she does not need help.

In one embodiment, data driven analyzers may be used to track the patient's habits. These data driven analyzers may incorporate a number of models such as parametric statistical models, non-parametric statistical models, clustering models, nearest neighbor models, regression methods, and engineered (artificial) neural networks. Prior to operation, data driven analyzers or models of the patient's habits or ambulation patterns are built using one or more training sessions. The data used to build the analyzer or model in these sessions are typically referred to as training data. As data driven analyzers are developed by examining only training examples, the selection of the training data can significantly affect the accuracy and the learning speed of the data driven analyzer. One approach used heretofore generates a separate data set referred to as a test set for training purposes. The test set is used to avoid overfitting the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, a number of different analyzers or models are built by presenting different parts of the training data as test sets to the analyzers in an iterative process. The parameter or model structure is then determined on the basis of the combined performance of all models or analyzers. Under the cross-validation approach, the analyzer or model is typically retrained with data using the determined optimal model structure.

In general, multiple dimensions of a user's daily activities such as start and stop times of interactions of different interactions are encoded as distinct dimensions in a database. A predictive model, including time series models such as those employing autoregression analysis and other standard time series methods, dynamic Bayesian networks and Continuous Time Bayesian Networks, or temporal Bayesian-network representation and reasoning methodology, is built, and then the model, in conjunction with a specific query makes target inferences.

Bayesian networks provide not only a graphical, easily interpretable alternative language for expressing background knowledge, but they also provide an inference mechanism; that is, the probability of arbitrary events can be calculated from the model. Intuitively, given a Bayesian network, the task of mining interesting unexpected patterns can be rephrased as discovering item sets in the data which are much more—or much less—frequent than the background knowledge suggests. These cases are provided to a learning and inference subsystem, which constructs a Bayesian network that is tailored for a target prediction. The Bayesian network is used to build a cumulative distribution over events of interest.

In another embodiment, a genetic algorithm (GA) search technique can be used to find approximate solutions to identifying the user's habits. Genetic algorithms are a particular class of evolutionary algorithms that use techniques inspired by evolutionary biology such as inheritance, mutation, natural selection, and recombination (or crossover). Genetic algorithms are typically implemented as a computer simulation in which a population of abstract representations (called chromosomes) of candidate solutions (called individuals) to an optimization problem evolves toward better solutions. Traditionally, solutions are represented in binary as strings of 0s and 1s, but different encodings are also possible. The evolution starts from a population of completely random individuals and happens in generations. In each generation, the fitness of the whole population is evaluated, multiple individuals are stochastically selected from the current population (based on their fitness), modified (mutated or recombined) to form a new population, which becomes current in the next iteration of the algorithm.

Substantially any type of learning system or process may be employed to determine the user's ambulatory and living patterns so that unusual events can be flagged.

In one embodiment, clustering operations are performed to detect patterns in the data. In another embodiment, a neural network is used to recognize each pattern as the neural network is quite robust at recognizing user habits or patterns. Once the treatment features have been characterized, the neural network then compares the input user information with stored templates of treatment vocabulary known by the neural network recognizer, among others. The recognition models can include a Hidden Markov Model (HMM), a dynamic programming model, a neural network, a fuzzy logic, or a template matcher, among others. These models may be used singly or in combination.

Dynamic programming considers all possible points within the permitted domain for each value of i. Because the best path from the current point to the next point is independent of what happens beyond that point. Thus, the total cost of [i(k), j(k)] is the cost of the point itself plus the cost of the minimum path to it. Preferably, the values of the predecessors can be kept in an M×N array, and the accumulated cost kept in a 2×N array to contain the accumulated costs of the immediately preceding column and the current column. However, this method requires significant computing resources. For the recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of user habit information against a given treatment model if the partial probability score for that comparison drops below a given threshold. This greatly reduces computation.

Considered to be a generalization of dynamic programming, a hidden Markov model is used in the preferred embodiment to evaluate the probability of occurrence of a sequence of observations O(1), O(2), . . . O(t), . . . , O(T), where each observation O(t) may be either a discrete symbol under the VQ approach or a continuous vector. The sequence of observations may be modeled as a probabilistic function of an underlying Markov chain having state transitions that are not directly observable. In one embodiment, the Markov network is used to model a number of user habits and activities. The transitions between states are represented by a transition matrix $A=[a(i,j)]$. Each $a(i,j)$ term of the transition matrix is the probability of making a transition to state j given that the model is in state i. The output symbol probability of the model is represented by a set of functions $B=[b(j) (O(t)]$, where the $b(j) (O(t))$ term of the output symbol matrix is the probability of outputting observation O(t), given that the model is in state j. The first state is always constrained to be the initial state for the first time frame of the utterance, as only a prescribed set of left to right state transitions are possible. A predetermined final state is defined from which transitions to other states cannot occur. Transitions are restricted to reentry of a state or entry to one of the next two states. Such transitions are defined in the model as transition probabilities. Although the preferred embodiment restricts the flow graphs to the present state or to the next two states, one skilled in the art can build an HMM model without any transition restrictions, although the sum of all the probabilities of transitioning from any state must still add up to one. In each state of the model, the current feature frame may be identified with one of a set of predefined output symbols or may be labeled probabilistically. In this case, the output symbol probability b(j) O(t) corresponds to the probability assigned by the model that the feature frame symbol is O(t). The model arrangement is a matrix A=[a(i,j)] of transition probabilities and a technique of computing B=b (j) O(t), the feature frame symbol probability in state j. The Markov model is formed for a reference pattern from a plurality of sequences of training patterns and the output symbol probabilities are multivariate Gaussian function probability densities. The patient habit information is processed by a feature extractor. During learning, the resulting feature vector series is processed by a parameter estimator, whose output is provided to the hidden Markov model. The hidden Markov model is used to derive a set of reference pattern templates, each template representative of an identified pattern in a vocabulary set of reference treatment patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator. The HMM template has a number of states, each having a discrete value. However, because treatment pattern features may have a dynamic pattern in contrast to a single value. The addition of a neural network at the front end of the HMM in an embodiment provides the capability of representing states with dynamic values. The input layer of the neural network comprises input neurons. The outputs of the input layer are distributed to all neurons in the middle layer. Similarly, the outputs of the middle layer are distributed to all output states, which normally would be the output layer of the neuron. However, each output has transition probabilities to itself or to the next outputs, thus forming a modified HMM. Each state of the thus formed HMM is capable of responding to a particular dynamic signal, resulting in a more robust HMM. Alternatively, the neural network can be used alone without resorting to the transition probabilities of the HMM architecture.

The system allows patients to conduct a low-cost, comprehensive, real-time monitoring of their vital daily life activities. Information can be viewed using an Internet-based website, a personal computer, or simply by viewing a display on the monitor. Data measured several times each day provide a relatively comprehensive data set compared to that measured during medical appointments separated by several weeks or even months. This allows both the patient and medical professional to observe trends in the data, such as a gradual increase or decrease in blood pressure, which may indicate a medical condition. The invention also minimizes effects of white coat syndrome since the monitor automatically makes measurements with basically no discomfort; measurements are made at the patient's home or work, rather than in a medical office.

To view information on daily life activities, the patient or an authorized third party such as family members, emergency personnel, or medical professional accesses a patient user interface hosted on the web server 200 through the Internet 100 from a remote computer system. The patient interface displays vital information such as ambulation, blood pressure and related data measured from a single patient. The system may also include a call center, typically staffed with medical professionals such as doctors, nurses, or nurse practioners, whom access a care-provider interface hosted on the same website on the server 200. The care-provider interface displays vital data from multiple patients.

The wearable appliance has an indoor positioning system and processes these signals to determine a location (e.g., latitude, longitude, and altitude) of the monitor and, presumably, the patient. This location could be plotted on a map by the server, and used to locate a patient during an emergency, e.g. to dispatch an ambulance.

In one embodiment, the web page hosted by the server 200 includes a header field that lists general information about the patient (e.g. name, age, and ID number, general location, and information concerning recent measurements); a table that lists recently measured blood pressure data and suggested (i.e. doctor-recommended) values of these data; and graphs that plot the systolic and diastolic blood pressure data in a time-dependent manner. The header field additionally includes a series of tabs that each link to separate web pages that include, e.g., tables and graphs corresponding to a different data measured by the wearable device such as calorie consumption/dissipation, ambulation pattern, sleeping pattern, heart rate, pulse oximetry, and temperature. The table lists a series of data fields that show running average values of the patient's daily, monthly, and yearly vital parameters. The levels are compared to a series of corresponding 'suggested' values of vital parameters that are extracted from a database associated with the web site. The suggested values depend on, among other things, the patient's age, sex, and weight. The table then calculates the difference between the running average and suggested values to give the patient an idea of how their data compares to that of a healthy patient. The web software interface may also include security measures such as authentication, authorization, encryption, credential presentation, and digital signature resolution. The interface may also be modified to conform to industry-mandated, XML schema definitions, while being 'backwards compatible' with any existing XML schema definitions.

The system provides for self-registration of Internet enabled appliances by the user. Data can be synchronized between the Repository and appliance(s) via the base station 20. The user can preview the readings received from the appliance(s) and reject erroneous readings. The user or treating professional can set up the system to generate alerts against received data, based on pre-defined parameters. The system can determine trends in received data, based on user defined parameters.

Appliance registration is the process by which a patient monitoring appliance is associated with one or more users of the system. This mechanism is also used when provisioning appliances for a user by a third party, such as a clinician (or their respective delegate). In one implementation, the user (or delegate) logs into the portal to select one or more appliances and available for registration. In turn, the base station server 20 broadcasts a query to all nodes in the mesh network to retrieve identification information for the appliance such as manufacturer information, appliance model information, appliance serial number and optionally a hub number (available on hub packaging). The user may register more than one appliance at this point. The system optionally sets up a service subscription for appliance(s) usage. This includes selecting service plans and providing payment information. The appliance(s) are then associated with this user's account and a control file with appliance identification information is synchronized between the server 200 and the base station 20 and each appliance on initialization. In one embodiment, each appliance 8 transmits data to the base station 20 in an XML format for ease of interfacing and is either kept encrypted or in a non-readable format on the base station 20 for security reasons.

The base station 20 frequently collects and synchronizes data from the appliances 8. The base station 20 may use one of various transportation methods to connect to the repository on the server 200 using a PC as conduit or through a connection established using an embedded modem (connected to a phone line), a wireless router (DSL or cable wireless router), a cellular modem, or another network-connected appliance (such as, but not limited to, a web-phone, video-phone, embedded computer, PDA or handheld computer).

In one embodiment, users may set up alerts or reminders that are triggered when one or more reading meet a certain set of conditions, depending on parameters defined by the user. The user chooses the condition that they would like to be alerted to and by providing the parameters (e.g. threshold value for the reading) for alert generation. Each alert may have an interval which may be either the number of data points or a time duration in units such as hours, days, weeks or months. The user chooses the destination where the alert may be sent. This destination may include the user's portal, e-mail, pager, voice-mail or any combination of the above.

Trends are determined by applying mathematical and statistical rules (e.g. moving average and deviation) over a set of reading values. Each rule is configurable by parameters that are either automatically calculated or are set by the user.

The user may give permission to others as needed to read or edit their personal data or receive alerts. The user or clinician could have a list of people that they want to monitor and have it show on their "My Account" page, which serves as a local central monitoring station in one embodiment. Each person may be assigned different access rights which may be more or less than the access rights that the patient has. For example, a doctor or clinician could be allowed to edit data for example to annotate it, while the patient would have read-only privileges for certain pages. An authorized person could set the reminders and alerts parameters with limited access to others. In one embodiment, the base station server 20 serves a web page customized by the user or the user's representative as the monitoring center that third parties such as family, physicians, or caregivers can log in and access information. In another embodiment, the base station 20 communicates with the server 200 at a call center so that the call center provides all services. In yet another embodiment, a hybrid solution where authorized representatives can log in to the base station server 20 access patient information while the call center logs into both the server 200 and the base station server 20 to provide complete care services to the patient.

The server 200 may communicate with a business process outsourcing (BPO) company or a call center to provide central monitoring in an environment where a small number of monitoring agents can cost effectively monitor multiple people 24 hours a day. A call center agent, a clinician or a nursing home manager may monitor a group or a number of users via a summary "dashboard" of their readings data, with ability to drill-down into details for the collected data. A clinician administrator may monitor the data for and otherwise administer a number of users of the system. A summary "dashboard" of readings from all Patients assigned to the Administrator is displayed upon log in to the Portal by the Administrator. Readings may be color coded to visually distinguish normal vs. readings that have generated an alert, along with description of the alert generated. The Administrator may drill down into the details for each Patient to further examine the readings data, view charts etc. in a manner similar to the Patient's own use of the system. The Administrator may also view a summary of all the appliances registered to all assigned Patients, including but not limited to all appliance identification information. The Administrator has access only to information about Patients that have been assigned to the Administrator by a Super Administrator. This allows for segmenting the entire population of monitored Patients amongst multiple Administrators. The Super Administrator may assign, remove and/or reassign Patients amongst a number of Administrators.

In one embodiment, a patient using an Internet-accessible computer and web browser, directs the browser to an appropriate URL and signs up for a service for a short-term (e.g., 1 month) period of time. The company providing the service completes an accompanying financial transaction (e.g. processes a credit card), registers the patient, and ships the patient a wearable appliance for the short period of time. The registration process involves recording the patient's name and contact information, a number associated with the monitor (e.g. a serial number), and setting up a personalized website. The patient then uses the monitor throughout the monitoring period, e.g. while working, sleeping, and exercising. During this time the monitor measures data from the patient and wirelessly transmits it through the channel to a data center. There, the data are analyzed using software running on computer servers to generate a statistical report. The computer servers then automatically send the report to the patient using email, regular mail, or a facsimile machine at different times during the monitoring period. When the monitoring period is expired, the patient ships the wearable appliance back to the monitoring company.

Different web pages may be designed and accessed depending on the end-user. As described above, individual users have access to web pages that only their ambulation and blood pressure data (i.e., the patient interface), while organizations that support a large number of patients (nursing homes or hospitals) have access to web pages that contain data from a group of patients using a care-provider interface. Other interfaces can also be used with the web site, such as interfaces used for: insurance companies, members of a particular company, clinical trials for pharmaceutical companies, and e-commerce purposes. Vital patient data displayed on these web pages, for example, can be sorted and analyzed depending on the patient's medical history, age, sex, medical condition, and geographic location. The web pages also support a wide range of algorithms that can be used to analyze data once they are extracted from the data packets. For example, an instant message or email can be sent out as an 'alert' in response to blood pressure indicating a medical condition that requires immediate attention. Alternatively, the message could be sent out when a data parameter (e.g. systolic blood pressure) exceeds a predetermined value. In some cases, multiple parameters (e.g., fall detection, positioning data, and blood pressure) can be analyzed simultaneously to generate an alert message. In general, an alert message can be sent out after analyzing one or more data parameters using any type of algorithm. These algorithms range from the relatively simple (e.g., comparing blood pressure to a recommended value) to the complex (e.g., predictive medical diagnoses using 'data mining' techniques). In some cases data may be 'fit' using algorithms such as a linear or non-linear least-squares fitting algorithm.

In one embodiment, a physician, other health care practitioner, or emergency personnel is provided with access to patient medical information through the server 200. In one embodiment, if the wearable appliance detects that the patient needs help, or if the patient decides help is needed, the system can call his or her primary care physician. If the patient is unable to access his or her primary care physician (or another practicing physician providing care to the patient) a call from the patient is received, by an answering service or a call center associated with the patient or with the practicing physician. The call center determines whether the patient is exhibiting symptoms of an emergency condition by polling vital patient information generated by the wearable device, and if so, the answering service contacts 911 emergency service or some other emergency service. The call center can review falls information, blood pressure information, and other vital information to determine if the patient is in need of emergency assistance. If it is determined that the patient in not exhibiting symptoms of an emergent condition, the answering service may then determine if the patient is exhibiting symptoms of a non-urgent condition. If the patient is exhibiting symptoms of a non-urgent condition, the answering service will inform the patient that he or she may log into the server 200 for immediate information on treatment of the condition. If the answering service determines that the patient is exhibiting symptoms that are not related to a non-urgent condition, the answering service may refer the patient to an emergency room, a clinic, the practicing physician (when the practicing physician is available) for treatment.

In another embodiment, the wearable appliance permits direct access to the call center when the user pushes a switch or button on the appliance, for instance. In one implementation, telephones and switching systems in call centers are integrated with the home mesh network to provide for, among other things, better routing of telephone calls, faster delivery of telephone calls and associated information, and improved service with regard to client satisfaction through computer-telephony integration (CTI). CTI implementations of various design and purpose are implemented both within individual call-centers and, in some cases, at the telephone network level. For example, processors running CTI software applications may be linked to telephone switches, service control points (SCPs), and network entry points within a public or private telephone network. At the call-center level, CTI-enhanced processors, data servers, transaction servers, and the like, are linked to telephone switches and, in some cases, to similar CTI hardware at the network level, often by a dedicated digital link. CTI processors and other hardware within a call-center is commonly referred to as customer premises equipment (CPE). It is the CTI processor and application software is such centers that provides computer enhancement to a call center. In a CTI-enhanced call center, telephones at agent stations are connected to a central telephony switching apparatus, such as an automatic call distributor (ACD) switch or a private branch exchange (PBX). The agent stations may also be equipped with computer terminals such as personal computer/video display unit's (PC/VDU's) so that agents manning such stations may have access to stored data as well as being linked to incoming callers by telephone equipment. Such stations may be interconnected through the PC/VDUs by a local area network (LAN). One or more data or transaction servers may also be connected to the LAN that interconnects agent stations. The LAN is, in turn, typically connected to the CTI processor, which is connected to the call switching apparatus of the call center.

When a call from a patient arrives at a call center, whether or not the call has been pre-processed at an SCP, the telephone number of the calling line and the medical record are made available to the receiving switch at the call center by the network provider. This service is available by most networks as caller-ID information in one of several formats such as Automatic Number Identification (ANI). Typically the number called is also available through a service such as Dialed Number Identification Service (DNIS). If the call center is computer-enhanced (CTI), the phone number of the calling party may be used as a key to access additional medical and/or historical information from a customer information system (CIS) database at a server on the network that connects the agent workstations. In this manner information pertinent to a call may be provided to an agent, often as a screen pop on the agent's PC/VDU.

The call center enables any of a first plurality of physician or health care practitioner terminals to be in audio communication over the network with any of a second plurality of patient wearable appliances. The call center will route the call to a physician or other health care practitioner at a physician or health care practitioner terminal and information related to the patient (such as an electronic medical record) will be received at the physician or health care practitioner terminal via the network. The information may be forwarded via a computer or database in the practicing physician's office or by a computer or database associated with the practicing physician, a health care management system or other health care facility or an insurance provider. The physician or health care practitioner is then permitted to assess the patient, to treat the patient accordingly, and to forward updated information related to the patient (such as examination, treatment and prescription details related to the patient's visit to the patient terminal) to the practicing physician via the network 200.

In one embodiment, the system informs a patient of a practicing physician of the availability of the web services and referring the patient to the web site upon agreement of the patient. A call from the patient is received at a call center. The call center enables physicians to be in audio communication over the network with any patient wearable appliances, and the call is routed to an available physician at one of the physician so that the available physician may carry on a two-way conversation with the patient. The available physician is permitted to make an assessment of the patient and to treat the patient. The system can forward information related to the patient to a health care management system associated with the physician. The health care management system may be a healthcare management organization, a point of service health care system, or a preferred provider organization. The health care practitioner may be a nurse practitioner or an internist.

The available health care practitioner can make an assessment of the patient and to conduct an examination of the patient over the network, including optionally by a visual study of the patient. The system can make an assessment in accordance with a protocol. The assessment can be made in accordance with a protocol stored in a database and/or making an assessment in accordance with the protocol may include displaying in real time a relevant segment of the protocol to the available physician. Similarly, permitting the physician to prescribe a treatment may include permitting the physician to refer the patient to a third party for treatment and/or referring the patient to a third party for treatment may include referring the patient to one or more of a primary care physician, specialist, hospital, emergency room, ambulance service or clinic. Referring the patient to a third party may additionally include communicating with the third party via an electronic link included in a relevant segment of a protocol stored in a protocol database resident on a digital storage medium and the electronic link may be a hypertext link. When a treatment is being prescribed by a physician, the system can communicate a prescription over the network to a pharmacy and/or communicating the prescription over the network to the pharmacy may include communicating to the pharmacy instructions to be given to the patient pertaining to the treatment of the patient. Communicating the prescription over the network to the pharmacy may also include communicating the prescription to the pharmacy via a hypertext link included in a relevant segment of a protocol stored in a database resident on a digital storage medium. In accordance with another related embodiment, permitting the physician to conduct the examination may be accomplished under conditions such that the examination is conducted without medical instruments at the patient terminal where the patient is located.

In another embodiment, a system for delivering medical examination, diagnosis, and treatment services from a physician to a patient over a network includes a first plurality of health care practitioners at a plurality of terminals, each of the first plurality of health care practitioner terminals including a display device that shows information collected by the wearable appliances and a second plurality of patient terminals or wearable appliances in audiovisual communication over a network with any of the first plurality of health care practitioner terminals. A call center is in communication with the patient wearable appliances and the health care practitioner terminals, the call center routing a call from a patient at one of the patient terminals to an available health care practitioner at one of the health care practitioner terminals, so that the available health care practitioner may carry on a two-way conversation with the patient. A protocol database resident on a digital storage medium is accessible to each of the health care practitioner terminals. The protocol database contains a plurality of protocol segments such that a relevant segment of the protocol may be displayed in real time on the display device of the health care practitioner terminal of the available health care practitioner for use by the available health care practitioner in making an assessment of the patient. The relevant segment of the protocol displayed in real time on the display device of the health care practitioner terminal may include an electronic link that establishes communication between the available health care practitioner and a third party and the third party may be one or more of a primary care physician, specialist, hospital, emergency room, ambulance service, clinic or pharmacy.

In accordance with other related embodiment, the patient wearable appliance may include establish a direct connection to the call center by pushing a button on the appliance. Further, the protocol database may be resident on a server that is in communication with each of the health care practitioner terminals and each of the health care practitioner terminals may include a local storage device and the protocol database is replicated on the local storage device of one or more of the physician terminals.

In another embodiment, a system for delivering medical examination, diagnosis, and treatment services from a physician to a patient over a network includes a first plurality of health care practitioner terminals, each of the first plurality of health care practitioner terminals including a display device and a second plurality of patient terminals in audiovisual communication over a network with any of the first plurality of health care practitioner terminals. Each of the second plurality of patient terminals includes a camera having pan, tilt and zoom modes, such modes being controlled from the first plurality of health care practitioner terminals. A call center is in communication with the patient terminals and the health care practitioner terminals and the call center routes a call from a patient at one of the patient terminals to an available health care practitioner at one of the health care practitioner terminals, so that the available health care practitioner may carry on a two-way conversation with the patient and visually observe the patient.

In one embodiment, the information is store in a secure environment, with security levels equal to those of online banking, social security number input, and other confidential information. Conforming to Health Insurance Portability and Accountability Act (HIPAA) requirements, the system creates audit trails, requires logins and passwords, and provides data encryption to ensure the patient information is private and secure. The HIPAA privacy regulations ensure a national floor of privacy protections for patients by limiting the ways that health plans, pharmacies, hospitals and other covered entities can use patients' personal medical information. The regulations protect medical records and other individually identifiable health information, whether it is on paper, in computers or communicated orally.

Figure 5:
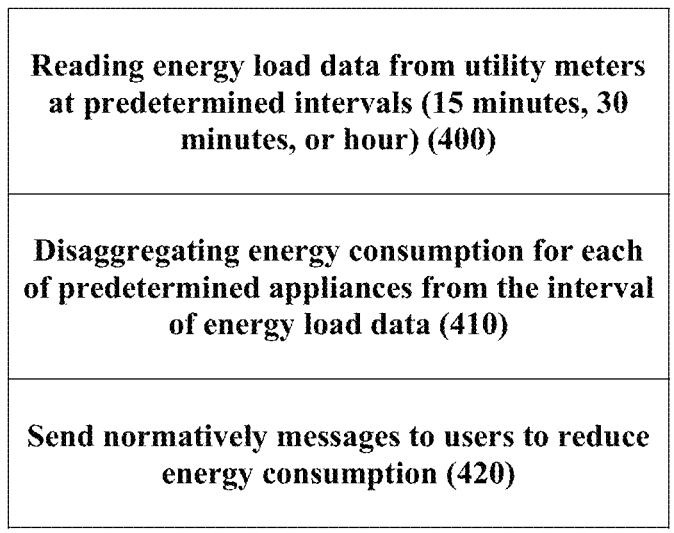
FIG. 5 shows an exemplary load disaggregation system working with hourly data to disaggregate appliance energy usage and to send messages to prompt users to save energy.

FIG. 5 shows an exemplary process to use NILM with hourly data. First, the process reads hourly energy load data from utility meters (400). Then the NILM engine disaggregates energy consumption for each of predetermined appliances from the hourly energy load data (410). Once the energy consumption has been disaggregated to show appliance energy usage data, the system can send normatively messages to users to reduce energy consumption (420).

In one embodiment, once the system has accurate energy usage models for the building and its occupants, the system applies normative messaging to successfully engage and motivate action across a very high percentage of targeted individuals. The normative message motivates office workers to take action which is one of the main challenges to achieving large scale energy savings. Participation rates in most energy-efficiency programs are typically less than 5%. By contrast, the messaging system achieves much higher energy-saving actions by presenting users with only relevant and immediately actionable suggestions on how to cut down power consumption in their immediate office/cubicle. The system leverages behavioral science, customer data analytics, and the latest software to engage employees of utilities and energy consumers to collectively take action to save energy. The system enables energy consumers to increase energy efficiency, reduce costs, and realize environmental benefits. The system can:

- Collect detailed occupancy/usage data with a combination of sub-meters and low cost sensors
- Create models of occupancy patterns (Daily Office Activities)
- Visualize usage data
- Apply occupancy models with sensor data to automatically control HVAC/heating/lighting/appliances to save energy
- Predict demand and communicate with utility computers during peak load
- Prompting of building occupants for energy-saving actions.

The system can compare a consumer's energy usage with similar energy consumption from his or her neighbors, and then select based on the comparison, a message to be provided to the consumer. The system can determine the relevant population that the consumer belongs to for comparison purposes. The relevant population can be based on geography, such as a city name, postal code, or both. The system can select a normative message from a plurality of candidate messages. The message selection can include assigning to each of at least a subset of a plurality of candidate messages a priority and selecting based at least in part on the assigned priorities a number of selected messages, wherein the number of messages selected corresponds to a limited number of messages to be presented to the consumer. The system can receive feedback indicative of an effectiveness of the message wherein the message is selected based at least in part on the feedback. Feedback data includes usage of at least the relevant population and the consumer. Feedback data includes consumer action taken with respect to the message. The system can determine usage of the resource as one or more of the following: a time-value curve, a mean usage, a median usage, an average usage, and an aggregate usage. The message to be provided to the consumer is part of the consumer's resource bill, the resource's website, or both.

The system can communicate a consumer's usage of an energy resource. First, a relevant group is determined. In some embodiments this may be omitted if a relevant member of the similar group is pre-calculated or determined externally. In some embodiments, determining the relevant group can include selecting the relevant group based at least in part on a determination that the consumer's usage of energy is greater than the relevant members of the similar group's usage of energy resource. Selecting the relevant members of the similar group can include comparing the consumer's usage to that of each of a plurality of candidate members of the similar groups and selecting as the relevant members of the similar group the candidate members of the similar group to which the consumer compares least favorably. In some embodiments, determining the relevant members of the similar group can include using third party data sources. For example, third party data sources may include records associated with home ownership, which are used to identify relevant members of the similar group based at least in part on information indicating such members own a home associated with their consumption of the resource. The consumer's usage and relevant members of the similar group's usage of the resource are compared. The usage of the resource may be time-value curve or a statistical measure such as a mean, median, average, or aggregate usage. In some embodiments, the usage is chosen at least in part so that the consumer's usage of the resource is greater than the relevant members of the similar group's usage of the resource. The comparison is communicated to the consumer. In some embodiments, the comparison is communicated to the consumer as integrated with the consumer's resource bill, standalone with the consumer's resource bill or on the resource's website under the consumer's web account.

Targeted direct marketing techniques can be used to persuade a consumer to moderate resource consumption using one or more of these techniques:

segmentation of the set of consumers into different subsets based upon a plurality of demographic variables;

segmentation of the set of consumers into different subsets based upon analysis and characterization of energy usage normalized to relevant peer groups;

prioritization of the messages based upon their historical rate of uptake multiplied by the expected energy savings value of the program;

offers and services for resource efficient products discounted by private industry through rebates, coupons, and other discounts to support government subsidies of efficient products;

high quality design (using high quality print design, high quality web graphics, video, audio and other multimedia) for all data reports, dynamically customized for each consumer;

integration with an Internet site or website for online and offline viewing of reports;

scalability of report format to hundreds of millions of reports;

enabling efficacy tracking of hundreds of simultaneous marketing and messaging campaigns; and straightforward integration with resource and/or utility databases.

In one example, a relevant group for a consumer could be "3-bedroom houses on the consumer's street". The system may have data that over a twelve month average, the consumer used 66% more electrical energy than the relevant group. Another example can include data that one or more members of the relevant group recently participated in a air conditioner efficiency rebate program, or that the consumer's electricity usage time-value curve coupled with a temperature time-value curve indicates that the consumer's electricity usage is higher than average during hot weather. In some embodiments, a similar analysis would determine whether a consumer's electricity usage increases as a percentage of daily use more than average during hot weather.

In some embodiments, the system can take a global list of possible candidate messages and filters out and prioritizes messages to be sent to the consumer. For example, the long global list of possible candidate messages may include a message to "install efficient central air conditioning using an existing government rebate", a message to "install a timer for a car engine block heater during winter". In the above example where the input data shows that a consumer's electricity usage is higher than average during hot weather, and that 39% of the relevant group members have participated in an air conditioner rebate program, the system may prioritize the "install efficient central air conditioning using an existing government rebate" candidate message higher than "install a timer for a car engine block heater during winter" candidate message, especially if another data indicates the consumer and relevant group members live in a state where there are no winters below freezing. Feedback is used to determine the effectiveness of the algorithms used in the messaging module to determine appropriate selected messages. In some embodiments, feedback includes usage of at least the relevant group members and the consumer, to see if any or no change has occurred since the last communication. In some embodiments, feedback includes consumer action taken with respect to the message, for example if a consumer has since participated in an air conditioner rebate program. In some embodiments, feedback includes an estimate of future usage of the relevant group and the consumer based on previous consumer action participation.

For utilities, the deployment of smart metering technology results in a flow of data several magnitudes greater than any previous traditional metering schemes. This increased data volume will not only flow into the managing utility, but may also be passed to and from third-party retailers for processing under new and modified market transactions. The need to manage this data, and subsequently transform it into actionable business intelligence, creates challenges for utilities implementing smart metering. To meet these challenges, in one embodiment, a load disaggregation meter data management systems provides utilities with a business-critical solution for storing, validating, aggregating and processing large volumes of data, in preparation for billing, settlements and other reporting and reconciliation obligations. In some markets, there will also be requirements for timely delivery of aggregated data to the market. In one embodiment, the system runs on a cloud computer that securely connects to a utility data center. In another embodiment, the system runs on a computer in the utility data center. The system provides "intelligence" that can be derived from smart meters and other smart grid devices so that utilities can derive the substantial benefits that smart grid deployments can deliver. As these deployments significantly increase data quantity & availability, the computer providing load disaggregation data analytics is essential.

The system accesses the utility's centralized data repository for meter readings. Adapters are provided to collection systems that enable raw data collected from smart meters to be loaded into the load disaggregator, while also enabling controls to be performed. The load disaggregator allows meter read management components to validate, estimate, edit (VEE) and apply utility-specific or regulation specific business logic to meter readings. An engine is provided to calculate energy usage, demand and other bill determinants. Adapters are provided to link in to downstream systems that consume processed meter data, such as billing, settlements, load forecasting, asset management and customer Web portals.

Emerging trends, such as demand response and distributed generation, introduce potential complexities in meter data management and billing that may expand the capabilities required from utility data centers. For instance, the need to support residential demand-response programs may require the ability to evaluate customer participation using: Demand-response event information; Customer override of load control reported by in-home devices; Customer baseline calculations using sophisticated methodologies that compare a number of similar nonevent days adjusted for weather; ability to perform "net settlement" functions (whereby the consumer is compensated for energy delivered onto the grid using a separate generation tariff). Distributed generation programs will also require additional capabilities. Allowing homes, farms and businesses to generate their own power from renewable sources, (such as wind, water, solar and agricultural biomass) and distributing any excess electricity back to the grid for credit will require: The ability to meter and store at least two channels of energy interval data (import and export values) for all customers. Net metering (consumer is billed for net energy use during the various tiers). Validation and estimation routines can account for energy imports from customers (and can accommodate negative net energy usage in an interval). Association of generation pricing tariffs to customer accounts. Utilities whose business drivers include billing, customer service and efficacy analysis for their demand-response and distributed generation programs can use the load disaggregation computer to provide these benefits.

The load disaggregation computer can handle widespread propagation and/or concentration of distributed generation on the distribution network. For example, utility support programs allowing homes, farms and businesses to generate their own power from renewable sources—wind, water, solar power, agricultural biomass—and send excess electricity back to the grid for credit, and the eventual mass adoption of plug-in electric vehicles that can act as distributed generation resources during peak periods. These diverse distributed generation resources typically use inverter-based technologies. Large concentrations, defined by some industry studies 3,4 as more than 10 percent of serviced premises on a feeder, or propagation of distributed generation on rural, low-density feeders, can result in a variety of problems around power Integration of distributed generation.

The system allows the smart meter network to act as the communications network required to create and implement a smarter distribution grid. New devices, such as transformer and feeder meters, are becoming integral elements of smart grid deployments. Utilities may also need to track in-home devices, such as thermostats 142 and load control switches—which may not be the utility's own assets—and their life cycles, as part of device and configuration management. Furthermore, many of these new devices are expected to be capable of remote configuration and reprogramming. The load disaggregator can work with grid monitoring equipment, such as transformer meters and feeder meters, to enable utilities to maintain accurate information about the distribution network hierarchy.

In the context of bi-directional smart metering infrastructure networks, the load disaggregator can act as the routing and management component for implementing two-way processes. For example, the system can provide "turn-on/turn-off" processes at a utility using a combination of manual processes and smart meters with an integrated remote connect disconnect (RCD) switch. In this case, once the load disaggregator and a customer information system determine that customer power is to be turned off, the system can determine, depending on the meter type, whether the turn-on/turn-off requires a field service order, or can be executed directly through the smart metering infrastructure systems. Other examples of process automation enabled by the load disaggregator include: On-demand reads initiated by customer service; Outage pings; Smart meter configuration and firmware upgrade management; Demand-response event orchestration and management. For exception monitoring, reporting and management, the system can subscribe to events, status messages, alarms and alerts from automated metering infrastructure to provide real-time monitoring of the network and field devices. The information provided can generate insight into operational issues, the health of devices and analysis of operational trends. Examples include: Use of reported meter health events to dispatch meter technicians to the field and review trends that may indicate quality issues with a particular batch or type of meter; Detection of tamper and theft from "unexpected" tilt indicators; Analysis of momentary outage indicators reported by meters on a distribution feeder or secondary to identify the need for vegetation trimming; Integration with intrusion detection systems to notify a potential security breach in the smart metering infrastructure network (such as unauthorized access at the meter's optical probe); and Calculation and reporting of reliability indices from smart meter outage and restoration information.

The system provides advanced asset management which is the ability to manage the operational state and performance of assets on the distribution network. By combining information about the distribution network topology with data from new smart-grid devices—such as transformer meters, low-voltage and medium voltage sensors (feeder meters) and metered data from smart meters and grid sensors—utilities can develop a wide array of monitoring, analytical and visualization applications. In combination with load disaggregation, these applications provide the distribution control center with a much higher degree of situational awareness. Distribution system planning groups can also use the same information to achieve a number of benefits. These include understanding the operational characteristics (such as loading, losses, phase imbalance and utilization) of the distribution network assets, optimizing the utilization of existing assets and the ability to defer capital expenditure for new assets. The load disaggregation thus can provide the ability to track grid assets, network hierarchy and data reported by grid devices.

The system allows utilities to offer additional products and services such as providing a low-cost, comprehensive, realtime monitoring of customer's vital daily life activities. Information can be viewed using an Internet-based website, a personal computer, or simply by viewing a display on the monitor. Data measured several times each day provide a relatively comprehensive data set compared to that measured during medical appointments separated by several weeks or even months.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A system for detecting individual appliance energy loads from a building composite load profile, comprising:
    an electric meter to capture building composite load profile;
    a detector coupled to the electric meter to detect transitions in the load profile to determine an appliance state machine for each appliance;
    a clusterizer to detect clusters of patterns in the load profile; and
    an analyzer coupled to the detector to receive the transitions and appliance state machines from the detector, the analyzer matching each transition to a predetermined appliance state machine to disaggregate the building composite load profile into individual appliance energy loads, wherein the analyzer sends messages on energy saving to a consumer based on predetermined weather factors and a prior success history of the message with a predetermined group members and captures feedback on the sent messages to see if a change has occurred since a communication, wherein the feedback includes a user action taken with respect to the message; and presenting to the user cost savings based on the user action.

2. The system of claim 1, wherein the analyzer receives non-electrical information to supplement assigning transitions to specific state machines.

3. The system of claim 1, wherein the electric meter comprises a utility smart meter and the analyzer comprises a processor in communication with the utility meter.

4. The system of claim 2, wherein the non-electrical information includes third party data and user input.

5. The system of claim 2, wherein the non-electrical information includes household square footage; household occupancy, temperature data, heating degree days, cooling degree days, neighborhood data, and municipality data.

6. A method for detecting individual appliance energy loads from a building composite load profile, comprising:
    determining transitions within the building composite load profile;
    clusterizing patterns in the load profile and determining specific appliance state machines for each appliance in the building based on the clusterized patterns; and
    disaggregating the building composite load profile into individual appliance energy loads by assigning the determined transitions to the determined specific appliance state machines;
    sending messages on energy saving to a consumer based on predetermined weather factors and a prior success history of the message with a predetermined group members;
    capturing feedback on the sent messages to see if a change has occurred since a communication, wherein the feedback includes a user action taken with respect to the message; and
    presenting to the user cost savings based on the user action.

7. The method of claim 6, wherein the transitions are determined by clustering data into one or more groups.

8. The method of claim 6, wherein the transitions are assigned based in part on non-electrical information used to assist in properly assigning transitions to the appropriate state machines.

9. The method of claim 6, wherein the disaggregating the building composite load profile comprises assigning the determined transitions based upon one or more rules selected from the group consisting of:
    (i) assigning transitions to only one state machine; and
    (ii) assigning transitions active state machines over non-active state machines.

10. The method of claim 6, comprising:
    determining an appliance load signature from a user's existing appliance from a building composite load signature;
    determining a substitute appliance for the existing appliance; and
    presenting to the user cost savings between the user's existing appliance and the substitute appliance.

11. The method of claim 6, further comprising generating an incentive for the user based at least in part on the difference in energy usage and difference in costs between the user's existing appliance and the substitute appliance.

12. The method of claim 6, further comprising identifying heat usage and air conditioning usage from a thermostat.

13. The method of claim 6, comprising suggesting actions to take to reduce energy consumption or recommending changes to air conditioning or heating appliances based on the disaggregated energy consumption to save energy.

14. The method of claim 6, comprising performing adaptive daily life activity tracking of a user's new activities or habits, making an assessment in accordance with a protocol and permitting a physician to prescribe a treatment, permitting the physician to refer the patient to a third party for treatment via an electronic link in a relevant segment of the protocol, communicating a prescription over the network to a pharmacy or communicating the prescription over the network to the pharmacy.

15. The method of claim 6, comprising mailing users to engage in energy saving and motivating action from users.

16. The method of claim 6, comprising deriving from utility meter readings energy usage for air conditioning, air heating, refrigerating, lighting, or water heating.

17. The method of claim 6, comprising predicting energy usage and performing demand response in accordance with the predicted energy usage.

18. The method of claim 6, comprising segmenting consumers into different subsets based upon a plurality of demographic variables; segmenting consumers into different subsets based upon energy usage normalized to relevant peer groups; prioritizing messages based upon a historical rate of uptake multiplied by expected energy savings value; offering resource efficient products discounted by private industry through rebates, coupons, and discounts for government subsidies of efficient products; integrating with an Internet website for online and offline viewing of reports; integrating with resource or utility databases; combining information about a distribution network topology with data from smart-grid devices including as transformer meters, low-voltage and medium voltage sensors and metered data from smart meters and grid sensors for situational awareness, loading, losses, phase imbalance and utilization of the distribution network assets, optimizing utilization of existing assets to defer capital expenditure for new assets.

19. The method of claim 6, comprising performing adaptive daily life activity tracking to adjust to a user's new activities or habits, flagging sudden changes for follow up and prompting a call center agent to follow up with the user to make sure he or she does not need help, where the tracking uses one or more models including parametric statistical models, non-parametric statistical models, clustering models, nearest neighbor models, regression methods, artificial neural networks.

20. The method of claim 8, wherein the non-electrical information includes third party data and user input.

* * * * *